United States Patent [19]

Pollock et al.

[11] Patent Number: 4,863,900

[45] Date of Patent: * Sep. 5, 1989

[54] METHOD FOR REDUCING VIRAL TRANSMISSION WITH POLY-L-HISTIDINE

[75] Inventors: Jerry J. Pollock, Nesconset, N.Y.; John J. Docherty, State College, Pa.

[73] Assignee: The Research Foundation of State University of New York, Albany, N.Y.

[*] Notice: The portion of the term of this patent subsequent to Feb. 16, 2005 has been disclaimed.

[21] Appl. No.: 3,621

[22] Filed: Jan. 15, 1987

[51] Int. Cl.$^4$ .................. A61K 37/02; C07K 7/10
[52] U.S. Cl. ...................................... 514/12; 514/21; 514/967; 514/968; 424/54
[58] Field of Search ............... 514/21, 12; 424/54; 519/967, 968

[56] References Cited

U.S. PATENT DOCUMENTS 4,725,576  2/1988  Pollock et al. .................. 514/21 X

OTHER PUBLICATIONS

Chem. Abstr., vol. 103, (1985) 142549.
Chem. Abstr., vol. 76, (1972), 100228.
Crumpacker et al., Antimicrobial Agents & Chemotherapy, 15, 642 (1979).
De Clercq et al, Proc. Natl. Acad. Sci. USA, 76, 2947 (1979).
Kern et al., Antimicrobial Agents and Chemotherpay, 13, 344 (1978).

Primary Examiner—Howard E. Schain
Attorney, Agent, or Firm—Omri M. Behr

[57] ABSTRACT

A composition for reducing the transmissability of viral infection from a subject infected therewith which comprises a topically applicable, pharmaceutically acceptable carrier and a viricidally effective amount of a polypeptide of between 24 and 500 aminoacid residues comprising at least 24 residues of L-Histidine.

13 Claims, 6 Drawing Sheets

METHOD FOR REDUCING VIRAL TRANSMISSION WITH POLY-L-HISTIDINE

This invention was made with Government support under the National Institutes of Health awarded by contract 2S0RR0577808. The Government has certain rights in the invention.

BACKGROUND OF THE INVENTION

At the present time, there are a number of small molecular weight drugs which are either being used therapeutically or are currently being tested in antiviral chemotherapy. The majority of these drugs are derivatives of nucleosides which exert their antiviral effects by penetrating viral-infected mammalian cells and interfering inside the cell with nucleic acid synthesis. To date, the failures of antiviral chemotherapy can be attributed in part to a lack of selective toxicity in that both host and viral nucleic acid synthesis are inhibited by these antiviral agents. Because antiviral effects are a consequence of traversion of the mammalian cell membrane, clinical efficacy depends upon achieving effective antiviral concentrations at the site of infection; in particular, intracellular levels of the antiviral agent must be adequate (Lorian, *Antibiotics in Laboratory Medicine*, 2nd Edition, Williams and Wilkins Publishers, p. 359, 1986).

A much less popular approach to antiviral chemotherapy has been the use of peptides which by themselves are too large to penetrate mammalian cells but will react with the surface envelope of the virus and inhibit viral infectivity. In blocking the site on the virus which attaches to the plasma membrane receptor of the host mammalian cell, the peptides may irreversibly and directly inactivate virus particles.

Among the peptides tested for antiviral activity, both synthetic poly-L-lysine and poly-L-arginine have been shown to possess inhibitory activity against influenza, Newcastle disease, tobacco mosaic, poliomyelitis, and mumps viruses (Watson and Bloom, *Proc. Soc. Exptl. Biol. Med.*, 81, 29, 1952; Stahmann, et al., *J. Biol. Chem.*, 189, 45, 1951; Green and Stahman, *Proc. Soc. Exptl. Biol. Med.*, 83, 641, 1953; Katchalski, et al., *The Proteins*, p. 564, 1964). However, basic polyamino acids of either lysine or arginine have been shown to be toxic in mammals (Rubini, et al., *Proc. Soc. Exptl. Biol. Med.*, 82, 231, 1953; Mauersberger, et al., *Exptl. Pathol* (Jena), 13, 268, 1977; Takada, et al., *J. Pharmaceut. Sci.*, 71, 1410, 1982) making them unacceptable for human use. More recently, two of six natural peptides isolated from polymorphonuclear leukocytes and rich in the amino acids, cysteine and arginine, have been shown to display inactivating capability against Herpes simplex Virus Type 1 and other selected envelope viruses (Lehrer, et al., *J. Virol.*, 54, 467, 1985). Although these natural compounds would be favorably expected to exhibit minimal toxicity, they showed little peptide-mediated inactivation at pH 5 or 6 and viral inactivation was relatively slow and only effective when pHs were 7.4 or preferably higher. These peptides would therefore be of little or no use, for example, for prevention or treatment of Herpes viral mucosal infections in the mouth or vaginal cavity, or for topical treatment on the skin where the pH is acidic rather than alkaline. The mean pH of the saliva under the tongue when taken in 385 subjects was noted to be 5.97 (range 5.73–6.15) (Jenkins, *The Physiology and Biochemistry of the Mouth*, p. 301, 1978) while the vaginal pH has been reported to range from 3.0 to 6.1 (Karnaky, *Am. J. Surg.*, 101, 456, 1961). The secretions that accumulate on the skin's surface have been determined to be weakly acidic, pH of 4.5 to 5.5 (Weissman, *Drug Intell. Clin. Pharm.*, 8, 535, 1974). Azen (*Biochem. Genet.*, 16, 79, 1978) studied certain naturally occurring histidine-rich peptides of human saliva which contain up to 30% L-histidine; however, Azen reported that he found no inhibitory effect of these peptides against either DNA or RNA viruses in tissue culture experiments.

SUMMARY OF THE INVENTION

A composition is provided for reducing the transmissability of viral infection from a subject, suitably a first subject, infected therewith which may be applied to tissues of said subject, at or proximate to the location of tissue lesions caused by said infection. The composition comprises a topically applicable, pharmaceutically acceptable carrier and a viricidally effective amount of a polypeptide of between 24 and 500 amino acid residues comprising at least 24 residues of L-histidine. Suitably, the said peptide contains at least one sequence of at least 24 L-histidine residues, preferably only L-histidine residues. It is further preferred that the peptide contains from 24 to about 75 residues, which need not be only L-histidine, though this is preferred. The composition has a pH of below 7.

The polypeptide may be administered to an infected (first) subject to reduce the spread of the viral particles within said subject to another location, through an open lesion. Similarly said administration will reduce transmission to a second subject in contact with said first subject where the tissues of said second subject are likely to contact the tissues of said first subject proximate to the location of viral lesions on said first subject. Further, there may be prophylactic administration to the tissues of said second subject where such contact is contemplated.

It is desirable that the peptide has, and is applied at a pH of between about 3 and about 6.8, suitably at a pH of between about 5.0 and about 6.1.

The invention is of general applicability, however it is particularly effective in infections of the mucosa, such as eye infection, oral infection, and vaginal infection, viral infections of the non mucosal tissues, in particular, border areas such as the lips and rectum as well as the skin are considered within the scope of this invention.

All envelope viruses are considered within the scope of the invention, especially, but not limited to herpes simplex virus, suitably HSV1 or HSV2 virus.

Delivery may be by any conventional means, preferably topical means. In the case of oral administration, this would include dentrifices, mouthwashes, tooth pastes or gels, mouth sprays, breath freshener tablets, candies or chewable vitamins.

Vaginal or rectal administration may be by the usual carriers such as douches, foams, creams, ointments, jellies and suppositories, the longer lasting forms being preferred. Occular administration is preferably by ophthalmic ointments or solutions.

DESCRIPTION OF THE PREFERRED EMBODIMENTS ·

Poly-L-histidines are commercially available mixtures of histidine chains of various lengths, up to about 75 amino acid units, produced by the polymerization of N-carboxyanhydride of L-histidine in the presence of a primary or secondary amine.

The histidine oligomers are similarly commercially available and are produced by single unit build-up in accordance with standard peptide synthesis methodologies.

The compositions containing the polypeptides should contain, depending on the nature of the composition, between about 0.01 and 3% by weight of the polypeptide. The modes of administration are those well recognized in application to mucosal and other tissues. Thus, for example, there may be provided vaginal creams, suppositories or solutions comprising between 0.01 and 3%, suitably at the lower end of this range, by weight of the histidine containing material. Where the location of the lesions is apparently external, the cream may be gently massaged into the surrounding areas twice daily. When intravaginal use is recommended, approximately 5 grams of the cream should be injected using a conventional applicator high into the vaginal vault once or twice a day with administration continued for about 1 to about 4 weeks. It may be preferred to utilize vaginal suppositories which are similarly inserted high into the vaginal vault once or twice daily and treatment continued for the same period of time.

The histidine peptides may also be incorporated into vaginal douches, however, it should be borne in mind that for the treatment or prevention of vaginal infections continual and frequent administration is desirable, while in most cases douching once or twice daily for from one week to four weeks is usually contraindicated for other reasons.

A conventional toothpaste or gel may be formulated containing from about 10 to about 3000 milligrams of histidine peptide materials per approximately 100 grams of paste if about 2 grams of this paste or gel is applied in the conventional manner to the teeth from 1-3 times per day.

A mouth spray containing between about 10 and about 3,000 milligrams of the histidine peptide material per about 100 ml. of spray may be formulated. This material may be sprayed as an antiviral agent in 0.25 to 0.50 ml. aliquots onto the tooth and gingiva surfaces of each quadrant between 1 and 3 times per day.

If desired, a mouth wash formulation may be provided containing between about 100 to about 30,000 milligrams of histidine peptide material per 1,000 ml. of mouthwash.

A skin lotion may be formulated containing between about 10 and 3,000 mg. of histidine peptide per about 100 grams of lotion, said lotion being massaged into the affected or exposable area about twice daily.

In all formulations, it is desirable to provide for a pH of below 7, suitably 5-6.1, since the histidine peptides are most effective at this range.

While the invention is in no way considered to be limited thereto, compositions for oral use include toothpastes and gels, mouth sprays, mouthwashes, candies, lozenges, chewing gum, breath fresheners and multivitamin chewable tablets, occular compositions such as creams and solutions, vaginal and rectal compositions which include creams, suppositories, and vaginal deodorant solutions. Specific formulations for the foregoing, set forth in greater detail hereinbelow, are further illustrative of the nature of the present invention. The compositions are prepared using methods familar to those skilled in the art. It will be understood that modifications thereof obvious to those skilled in the art are to be included within the spirit and purview of this application and the scope of the appended claims.

MATERIALS AND METHODS

Antiviral Agents

Figure 1:
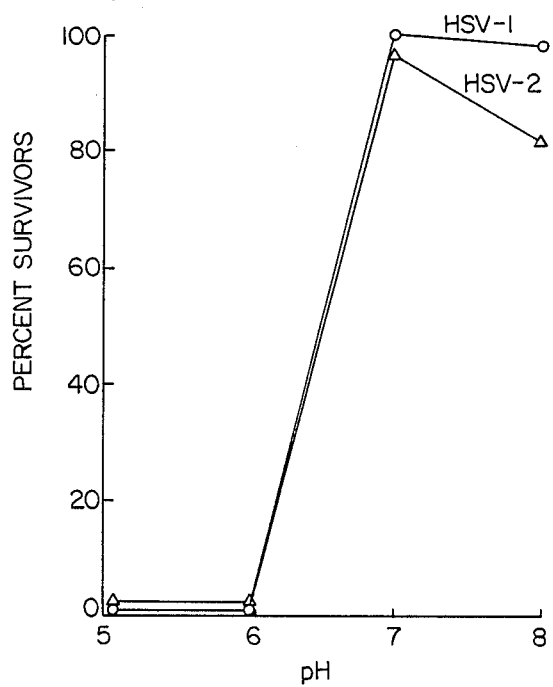
FIG. 1 is a plot showing the effect of His-75 polypeptide on HSV1 and HSV2 at various pH values.

Homologous polypeptides of L-Histidine containing 12, 18, and 24 amino acid residues with corresponding molecular weights of 1,665, 2,487 and 3,310 daltons were prepared specifically for the inventors by Peninsula Laboratories (California) using standard peptide syntheses methodologies.

Poly-L-Histidines of 64 residues (average molecular weight of 8,800 daltons) and of 75 residues (average molecular weight of 10,300 daltons) were commercially available from ICN Laboratories. The poly-L-histidines were prepared by polymerization of the N-carboxyanhydride of L-histidine in the presence of a primary or secondary amine.

EXAMPLE I

| Toothpaste (Gel Formulation) | |
| --- | --- |
| One of the following: | |
| Poly-L-Histidine (molecular weight greater than 2,500 daltons) | 10 mg. |
| Synthetic 24 Residue Peptide of L-Histidine | 10 mg. |
| and | |
| Carboxymethyl Cellulose | 1.8 gm. |
| Carbowax Polyethylene Glycol 600 (Union Carbide Corp.) | 15.0 gm. |
| Zeo-49 (Huber Co.)* | 38.0 gm. |
| Sodium Lauryl Sulfate | 1.5 gm. |
| Sodium Saccharin | 0.2 gm. |
| Sodium Benzoate | 0.5 gm. |
| Flavor** | 1.0 gm. |
| Water | 100.0 gm. |
| Adjust to pH 6 | |

Product is utilized as an antiviral preparation by cleaning teeth with about 1 and 2 gm of gel between 1 and 3 times per day.
*Sodium Aluminosilicate
**Examples of suitable flavoring constituents are flavoring oils, e.g., oils of spearment, peppermint, wintergreen, sassafras, clove, sage, eucalyptus, marjoram, cinnamon, lemon, orange and methylsalicylate.

EXAMPLE II

| Toothpaste (Cream Formulation | |
| --- | --- |
| One of the following: | |
| Poly-L-Histidine (molecular weight greater than 2,500 daltons) | 10 mg. |
| Synthetic 24 Residue Peptide of L-Histidine | 10 mg. |
| and | |
| Carboxymethyl Cellulose 120H | 1.8 gm. |
| Glycerin | 2.0 ml. |

| Toothpaste (Cream Formulation) | |
|---|---|
| Propylene glycol | 39.0 ml. |
| Purified Water | 27.0 ml. |
| Methyl paraben | 0.2 gm. |
| Saccharin sodium (50% sol.) | 0.2 ml. |
| Peppermint Oil | 0.6 ml |
| Mineral Oil | 2.0 ml. |
| Triton X-100 | 5.0 gm. |
| Dicalcium Phosphate | 21.0 gm. |
| Adjust to pH 6 | |

The formulation is utilized as an antiviral preparation by cleaning the teeth with about 1 to 2 gm. of the paste between 1 and 3 times per day.

EXAMPLE III

| Mouthwash Formulation | |
|---|---|
| One of the following: | |
| Poly-L-Histidine (molecular weight greater than 2,500 daltons) | 100 mg. |
| Synthetic 24 Residue Peptide of L-Histidine | 100 mg. |
| Thymol | 0.5 gm. |
| Eucalyptol | 1.0 gm. |
| Methyl Salicylate | 0.5 gm. |
| Ethyl Alcohol (95%) | 100.0 gm. |
| Glycerin | 100.0 gm. |
| Water | 1000.0 gm. |
| Adjust to pH 6 | |

The formulation is utilized as an antiviral preparation by rinsing the mouth for about 30–60 seconds from 1–3 times per day with 20 ml. of undiluted mouthwash.

EXAMPLE IV

| Mouth Spray | |
|---|---|
| One of the following: | |
| Poly-L-Histidine (molecular weight greater than 2,500 daltons) | 30 mg. |
| Synthetic 24 Residue Peptide of L-Histidine | 30 mg. |
| and | |
| Peppermint Spirit | 43.2 gm. |
| Saccharin Sodium | 0.07 gm. |
| Water | 300.0 gm |
| Adjust to pH 6 | |

The formulation is utilized as an antiviral preparation by spraying aliquots of 0.25 to 0.50 ml. onto the oral mucosal and tooth surfaces of each quadrant betweel 1 and 3 times a day.

EXAMPLE V

| Breath Freshener Tablet | |
|---|---|
| One of the following: | |
| Poly-L-Histidine (molecular weight greater than 2,500 daltons) | 0.1 mg. |
| Synthetic 24 Residue Peptide of L-Histidine | 0.1 mg. |
| and | |
| Wintergreen Oil | 0.6 mg. |
| Talc | 10.0 mg. |
| Menthol | 0.85 mg. |
| Peppermint Oil | 0.3 mg. |
| Mannitol USP (powdered) | 180.95 mg. |
| Sodium Stearate | 2.0 mg. |
| Sorbitol USP (powdered) | 180.0 mg. |

| Breath Freshener Tablet | |
|---|---|
| Lactose USP (powdered) (g.s.) | 1.0 gm. |

The formulation is utilized as an antiviral preparation as needed.

EXAMPLE VI

| Candy (Lozenge) | |
|---|---|
| One of the following: | |
| Poly-L-Histidine (molecular weight greater than 2,500 daltons) | 0.2 mg. |
| Synthetic 24 Residue Peptide of L-Histidine | 0.2 mg. |
| and | |
| Acacia | As required for binding |
| Mannitol (powdered) USP | 180.0 mg. |
| Sodium Saccharin | 1.1 mg. |
| Sodium Stearate | 5.0 mg. |
| Licorice | 98.0 mg. |
| Talc | 10.0 mg. |
| Capsicum | 2.0 mg. |
| Mentol | 1.8 mg. |
| Lactose (powdered) USP (q.s.) | 2.0 gm. |

The formulation is utilized as an antiviral preparation as needed.

EXAMPLE VII

| Chewing Gum | |
|---|---|
| One of the following: | |
| Poly-L-Histidine (molecular weight greater than 2,500 daltons) | 0.2 mg. |
| Synthetic 24 Residue Peptide of L-Histidine | 0.2 mg. |
| and | |
| Gum Base: | |
| Estergum | 142 mg. |
| Coumarine Resin | 213 mg. |
| Latex (dry) | 71 mg. |
| Paraffin Wax (melting pt. 180° F.) | 47 mg. |
| Corn Syrup (Baume 45° C.) | 400 mg. |
| Flavor | 20 mg. |
| Sorbitol (for sugarless gum (q.s.) | 2 gm. |

The formulation is utilized as an antiviral preparation as needed.

EXAMPLE VIII

| Chewable Multivitamin Tablet | |
|---|---|
| One of the following: | |
| Poly-L-Histidine (molecular weight greater than 2,500 daltons) | 0.1 mg. |
| Synthetic 24 Residue Peptide of L-Histidine | 0.1 mg. |
| and | |
| Vitamin A USP (dry stabilized form) | 5000 USP units |
| Vitamin D (dry stabilized form) | 400 USP units |
| Ascorbic Acid USP | 60.0 mg. |
| Thiamine HCl USP | 1.0 mg. |
| Riboflavin HCl | 1.5 mg. |
| Pyridoxine HCl USP | 1.0 mg. |
| Cyanocobalamin USP | 2.0 μg. |
| Calcium Pantothenate USP | 3.0 mg. |
| Niacinamide USP (granular) | 10.0 mg. |
| Mannitol USP (granular) | 236.2 mg. |
| Corn Starch | 16.6 mg. |
| Sodium Saccharin | 1.1 mg. |
| Sodium Stearate | 6.6 mg. |
| Talc | 10.0 mg. |

| Chewable Multivitamin Tablet | |
| --- | --- |
| Wintergreen Oil | 1.2 mg. |
| Menthol | 1.7 mg. |
| Peppermint Oil | 0.6 mg. |
| Lactose USP (powdered) (q.s.) | 1.0 gm. |

The formulation is utilized as an antiviral preparation by taking and chewing one tablet each day.

EXAMPLE IX

| Topical, Vaginal, or Rectal Cream | |
| --- | --- |
| One of the following: | |
| Poly-L-Histidine (molecular weight greater than 2,500 daltons) | 10 mg. |
| Synthetic 24 Residue Peptide of L-Histidine | 10 mg. |
| and | |
| Cetyl Alcohol | 0.5 gm. |
| Stearic Acid | 25.0 gm. |
| Sodium Lauryl Sulfate | 0.2 gm. |
| Glycerin | 10.0 gm. |
| Triethanolamine | 0.2 gm. |
| Methyl Paraben | 0.1 gm. |
| Propyl Paraben | 0.1 gm. |
| Water | 100 gm. |
| For Contraceptive use, add: | |
| Nonylphenoxypolyethoxy ethanol | 5.0 gm. |
| pH adjusted to 6 | |

For topical antiviral use, gently massage cream into the affected and surrounding areas of the skin, penis, lips, or oral mucosa, twice daily (morning and evening). For intravaginal or rectum antiviral use, apply about 5 gm. of cream with applicator high into the vaginal vault or rectum once or twice daily. Continue as indicated until lesions are no longer noted.

EXAMPLE X

| Vaginal or Rectal Suppositories | |
| --- | --- |
| One of the following: | |
| Poly-L-Histidine (molecular weight greater than 2,500 daltons) | 10 mg. |
| Synthetic 24 Residue Peptide of L-Histidine | 10 mg. |
| and | |
| Polyethylene Glycol 4000 | 25.0 gm. |
| Polyethylene Glycol 1000 | 35.0 gm. |
| Polysorbate 80 | 2.0 gm. |
| Glycerin | 25.0 gm. |
| Methyl Paraben | 0.1 gm. |
| Propyl Paraben | 0.1 gm. |
| Water | 100 gm. |
| For contraceptive use, add: | |
| Nonylphenoxypolyethoxy ethanol | 5.0 gm. |
| pH adjusted to 6 | |

Insert one 3 gm. suppository into the vaginal vault or rectum once or twice daily. Continue as indicated until lesions are no longer noted.

EXAMPLE XI

| Vaginal Deodorant Solution | |
| --- | --- |
| One of the following: | |
| Poly-L-Histidine (molecular weight greater than 2,500 daltons) | 10 mg. |
| Synthetic 24 Residue Peptide of L-Histidine | 10 mg. |
| and | |
| Sodium Acetate .3H$_2$O | 0.17 gm. |
| Acetic Acid | 0.07 ml. |
| Sodium Chloride | 0.88 gm. |
| Ethyl Alcohol (95%) | 5.0 ml. |
| Sodium Lauryl Sulfate | 0.5 gm. |
| Menthol | 0.25 gm. |
| Thymol | 0.25 gm. |
| Methyl Salicylate | 0.5 gm. |
| Water | 100 ml. |
| pH adjusted to 6 | |

Apply about 200 ml. daily to vaginal mucosal surfaces.

EXAMPLE XII

| Topical, Vaginal, or Rectal Ointment | |
| --- | --- |
| One of the following: | |
| Poly-L-Histidine (molecular weight greater than 2,500 daltons) | 100 mg. |
| Synthetic 24 Residue Peptide of L-Histidine | 100 mg. |
| and | |
| Methyl Paraben | 0.25 gm. |
| Propyl Paraben | 0.15 gm. |
| Sodium Lauryl Sulfate | 10.0 gm. |
| Propylene Glycol | 120.0 gm. |
| Stearyl Alcohol | 250.0 gm. |
| White Petrolatum | 250.0 gm. |
| Purified H$_2$O (q.s.) | 1000.0 gm. |
| For contraceptive use, add: | |
| Nonylphenoxypolyethoxy ethanol | 50.0 gm. |
| pH adjusted to 6 | |

For topical antiviral use, gently massage ointment into the affected and surrounding areas of the skin, penis, lips or oral mucosa, twice daily (morning and evening). For intravaginal or rectum antiviral use, apply about 5 gm. of ointment with applicator high into the vaginal vault or rectum once or twice daily. Continue as indicated until lesions are no longer noted.

EXAMPLE XIII

| Skin Lotion | |
| --- | --- |
| One of the following: | |
| Poly-L-Histidine (molecular weight greater than 2,500 daltons) | 10 mg. |
| Synthetic 24 Residue Peptide of L-Histidine | 10 mg. |
| and | |
| Propylene Glycol | 24.0 ml. |
| Triethanolamine | 1.0 ml. |
| Oleic Acid | 1.5 ml. |
| Polyethylene Glycol 400 Monostearate | 10.5 gm. |
| Silicone Fluid | 10.0 ml. |
| Carbopol | 50.0 gm. |
| Water (q.s.) | 100.0 ml. |
| pH adjusted to 6 | |

For topical antiviral use, gently massage lotion into the affected and surrounding areas of the skin, penis or lips twice daily (morning and evening). Continue as indicated until lesions are no longer noted.

EXAMPLE XIV

| Vaginal Jelly | |
|---|---|
| One of the following: | |
| Poly-L-Histidine (molecular weight greater than 2,500 daltons) | 10 mg. |
| Synthetic 24 Residue Peptide of L-Histidine | 10 mg. |
| and | |
| Ricinoleic Acid | 0.5 gm. |
| Hexylresorcinol | 0.1 gm. |
| Chlorothymol | 0.01 gm. |
| Oxyquinoline Sulfate | 0.025 gm. |
| Boric Acid | 3.0 gm. |
| Glycerin | 5.0 gm. |
| Propylparaben | 10.0 gm. |
| Methylparaben | 50.0 mg. |
| Tragacanth | 7.0 gm. |
| Acacia | 3.0 gm. |
| Water | 100.0 gm. |
| For contraceptive use, add: | |
| Nonylphenoxypolyethoxy ethanol | 5.0 gm. |
| pH adjusted to 6 | |

For intravaginal use, apply about 5 gm. of jelly with applicator high into the vaginal vault once or twice daily. Continue as indicated until lesions are no longer noted.

EXAMPLE XV

| Vaginal Foam | |
|---|---|
| One of the following: | |
| Poly-L-Histidine (molecular weight greater than 2,500 daltons) | 10 mg. |
| Synthetic 24 Residue Peptide of L-Histidine | 10 mg. |
| and | |
| Isobutane and Propane (Propellant A-46) | 5.0 gm. |
| Laureth 4 (polyethylene glycol ether of lauryl alcohol) | 0.2 ml. |
| Cetyl Alcohol | 4.0 ml. |
| Poloxamer 188 (polyoxyethylene, polypropylene block polymer) | 0.2 gm. |
| Polyethylene Glycol | 0.3 gm. |
| Imidazole Buffer, pH 6.0 (q.s.) | 100 ml |
| For contraceptive use, add: | |
| Nonylphenoxypolyethoxy ethanol | 5.0 gm. |

For intravaginal use, dispense sufficient foam once or twice daily to line the entire vaginal vault. Continue as indicated until lesions are no longer noted.

EXAMPLE XVI

| Ophthalmic Ointment | |
|---|---|
| One of the following: | |
| Poly-L-Histidine (molecular weight greater than 2,500 daltons) | 0.1 mg. |
| Synthetic 24 Residue Peptide of L-Histidine | 0.1 mg. |
| and | |
| Methylparaben | 0.5 mg. |
| Propylparaben | 0.1 mg. |
| Benzalkonium Chloride | 0.25 mg. |
| Sorbitan Monolaurate | 20.0 mg. |
| White Petrolatum | 250.0 mg. |
| Purified H$_2$O (q.s.) | 1.0 gm. |
| Adjust to pH 6 | |

For antiviral use, apply a small amount to the eye(s) four times daily and at bedtime until lesions are no longer noted.

EXAMPLE XVII

| Ophthalmic Solution | |
|---|---|
| One of the following: | |
| Poly-L-Histidine (molecular weight greater than 2,500 daltons) | 0.1 mg. |
| Synthetic 24 Residue Peptide of L-Histidine | 0.1 mg. |
| and | |
| Sodium Thiosulfate | 3.1 mg. |
| Methylcellulose | 5.0 mg. |
| Methylparaben | 0.5 mg. |
| Propylparaben | 0.1 mg. |
| Imidazole Buffer, pH 6.0 (q.s.) | 1.0 ml. |
| Filter sterilize | |

For antiviral use, instill one or two drops into the eye(s) four times daily and at bedtime until lesions are no longer noted.

EXAMPLE XVIII

Test Procedures

The effect of His-75 (poly-L-Histidine) on the inactivation of HSV1 and HSV2 was investigated. The polypeptide at 100 µg/ml. was mixed with approximately 10$^5$ plaque forming units of either virus type and incubated 1 hour at 37° C. Controls were treated identically but were incubated without the peptide. Surviving virus was determined by the plaque assay (Docherty, et al., *Proc. Soc. Exp. Biol. Med.*, 136, 328, 1971) and percent survivors was established by the following formula:

$$\frac{\text{(pfu treated virus)}}{\text{(pfu control virus)}} \times 100$$

The results presented in FIG. 1 demonstrate that both HSV1 and HSV2 were inactivated at pH 5 and 6 but not at pH 7 and 8. Some small amount of inactivation at pH 8 for HSV2 was recorded but this value was not reproducible.

EXAMPLE XIX

Figure 2:
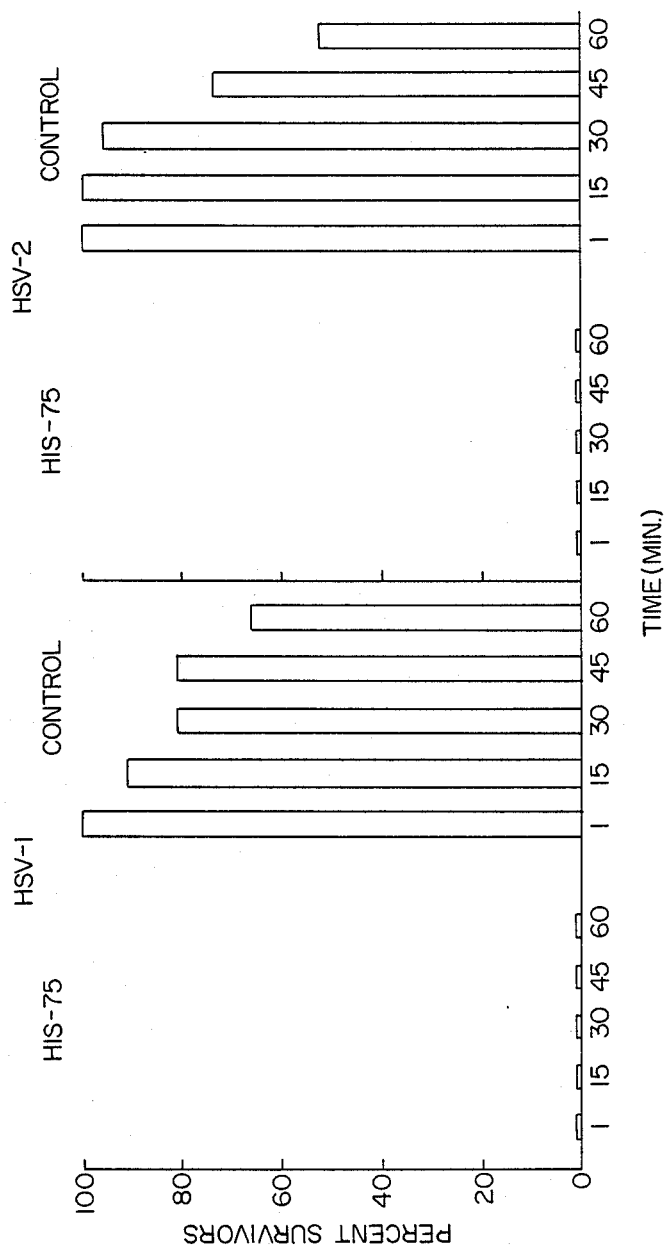
FIG. 2 is a bar graph plot showing the effect of the His-75 polypeptide on the viability of HSV1 and HSV2 at pH 6.0 over various time exposures as compared to controls not so exposed.

To determine the length of time required for inactivation of HSV1 and HSV2 by 100 µg/ml. of His-75 at 37° C., the standard assay was set up as described but samples were taken at 1, 15, 30, 45 and 60 minutes. Control virus was treated in an identical manner but not exposed to His-75. As presented in FIG. 2, it is clear that both HSV1 and HSV2 are inactivated by as little as one minute of exposure to the drug, as well as 15, 30, 45, and 60 minutes. Indeed, the viruses may be inactivated within seconds of exposure to the drug but the mechanics of the virus inactivation assay system prevented testing for infectious virus more rapidly. Control preparations held under identical conditions (minus His-75) show minor loss of infectivity with time which was anticipated.

EXAMPLE XX

Figure 3:
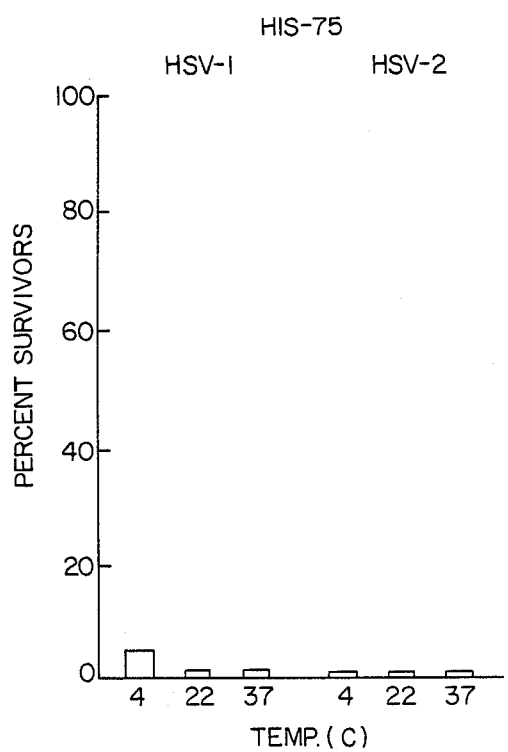
FIG. 3 is a bar graph showing the effect of temperature on the His-75 activation of HSV1 and HSV2.

Temperature effects on inactivation by His-75 was investigated. The assay system as described using 100 µg/ml. of His-75 was set up at pH 6.0. The His-75 samples were placed at 4° C., 22° C., and 37° C. prior to addition of HSV1 and HSV2. The reaction proceeded for 1 hour prior to the plaque assay to determine the percentage of survivors. The data presented in FIG. 3 demonstrate that for both HSV1 and HSV2, inactivation was almost complete at most temperatures. However, at 4° C. a small amount of HSV1 survived.

EXAMPLE XXI

Figure 4:
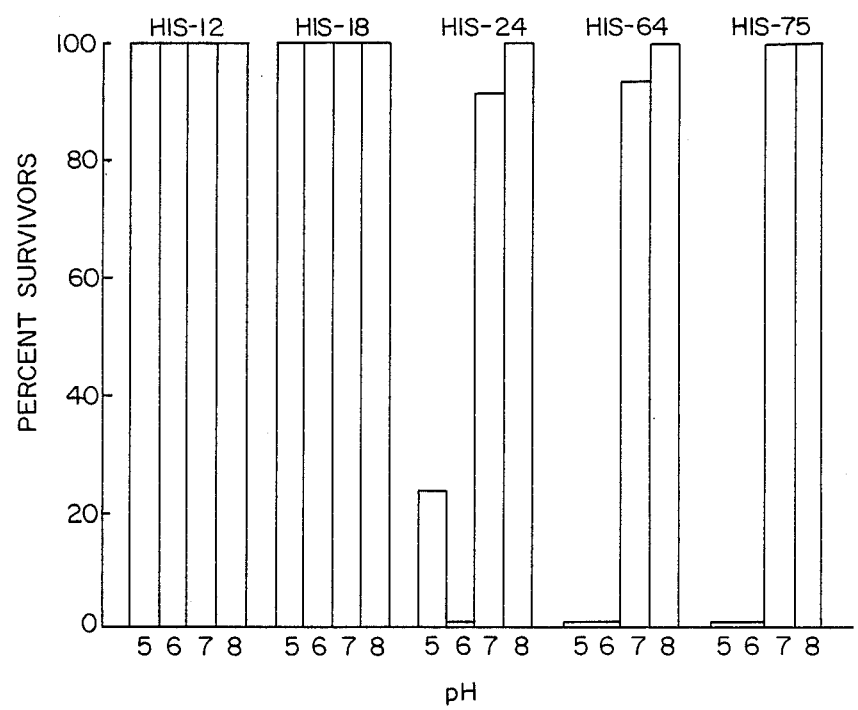
FIG. 4 is a bar graph of the relationship of pH and peptide chain length on the inactivation of HSV1 and HSV2.

The effect of poly-L-histidine chain length on the inactivation of HSV1 was investigated at pH 5, 6, 7, 8. His-12, His-18, His-24, His-64, and His-75 at 100 μg/ml. were incubated with approximately $10^5$ pfu of HSV1 for 1 hour at 37° C. at the 4 different pHs. Control preparations only lacked the peptide. Surviving virus was calculated by the plaque assay and percent survivors calculated. The results in FIG. 4 revealed that His-12 and His-18 were ineffective at all 4 pHs tested. His-24 at pH 6 efficiently inactivated HSV1 and at pH 5.0 inactivated approximately ¾ of the virus present. At pH 7 approximately 10% of the virus was inactivated while at pH 8 no inactivation took place. His-64 inactivated HSV1 at pH 5 and 6. Some minor inactivation occurred at pH 7 and none at pH 8. His-75 the prototype preferred peptide efficiently inactivated HSV1 at pH 5 and 6 but not at pH 7 not lid 8.

Figure 5:
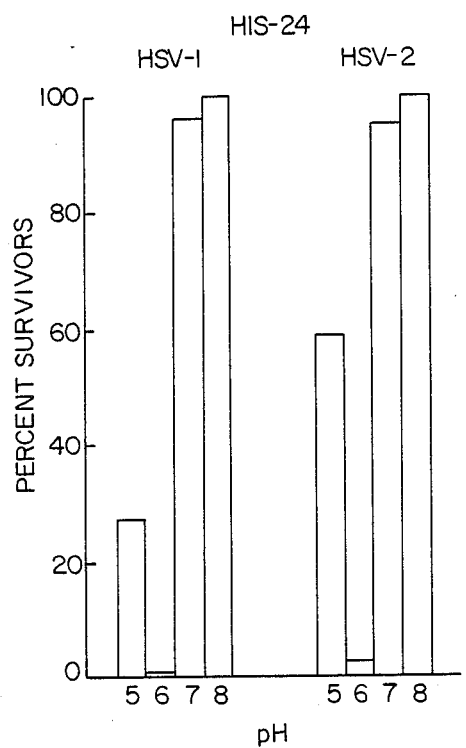
FIG. 5 is a bar graph of the relationship of pH on inactivation of HSV1 and HSV2 by His 24.

Although His-24 was the smallest poly-L-histidine to show activity on HSV1, its activity on HSV2 was unknown. Therefore, the effect of His-24 on HSV2 was tested and compared to HSV1. The standard assay was set up with 100 μg/ml. of His-24 at pH 5, 6, 7 and 8 and incubated one hour at 37° C. Surviving virus was determined by the plaque assay and percent survivors calculated. FIG. 5 reveals the His-24 was effective on both HSV1 and HSV2 at pH 6 and somewhat effective at pH 5. At pH 7 and 8, very little to no inactivation occurred.

EXAMPLE XXII

While 100 μg/ml. of His-75 was routinely used in the inactivation assay it was desirable to establish the range of drug concentrations that would inactivate HSV1 or HSV2. His-75 at 0.1, 1, 10, and 100 μg/ml. at pH 6.0 were mixed with approximately $10^5$ pfu of virus for one hour at 37° C. Control preparations lacked His-75. Surviving virus was established by the plaque assay and percent survivors calculated. Table 1 reveals that at 100 μg/ml. of His-75 no virus survived while at 10 μg/ml. 64% and 84% of HSV1 and HSV2 respectively survived. At 1 μg/ml. 83% of HSV1 survived and 62% of HSV2 survived. When 0.1 μg/ml. was used neither virus was inactivated.

Figure 6:
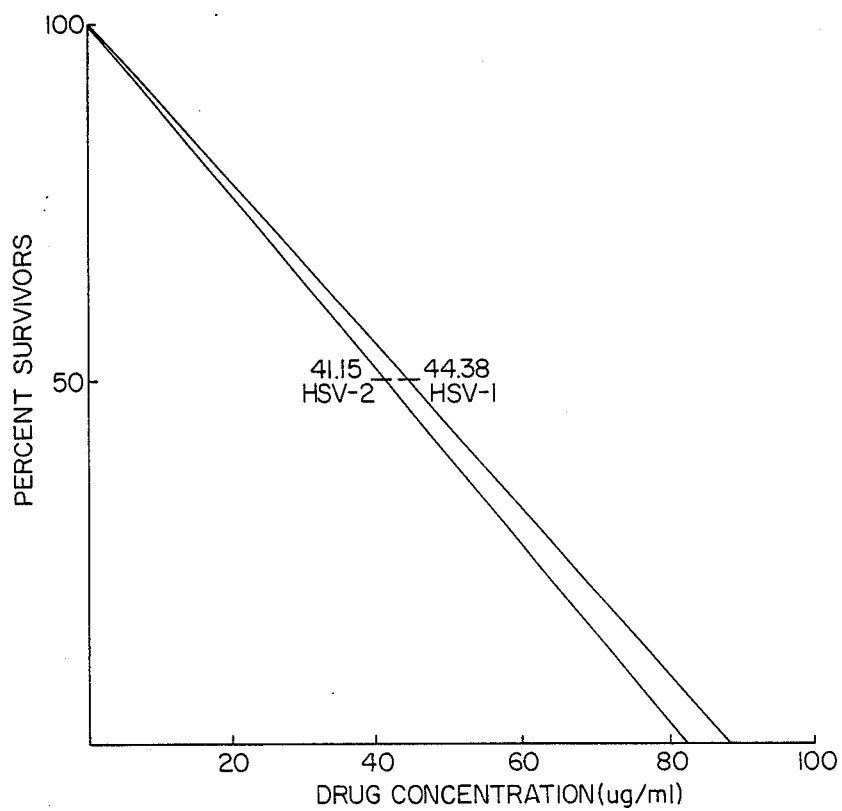
FIG. 6 is an $ID_{50}$ plot of His-75 effect on HSV1 or HSV2.

To calculate the $ID_{50}$ (amount of drug required to inactivate 50% of the virus) data was analyzed by linear regression analysis. The results in FIG. 6 established that the $ID_{50}$ of His-75 for HSV1 was 44.38 μg/ml. and for HSV2 41.15 μg/ml.

EXAMPLE XXIII

Attempts at reversing the effects of the peptides after inactivation by increasing the pH were made. HSV1 was incubated with 100 μg/ml. of His-75 at pH 6.0 for 30 minutes at 37° C. The pH of the solution was rapidly elevated to pH 7.2 (a pH at which His-75 does not inactivate HSV) for an additional 30 minutes prior to assaying for infectious virus by the plaque assay. Controls included virus held with His-75 at pH 6.0 at 37° C. for 60 and 30 minutes and not shifted to pH 7.2 prior to the plaque assay. Additional controls included virus treated as above but not in the presence of His-75. The results in Table 2 demonstrate that the inactivation was not reversed by elevating the pH. The initial inactivation is apparently permanent and irreversible.

EXAMPLE XXIV

1. HSV1 ($4.4 \times 10^6$ plaque forming units) was incubated with 100 μg. of poly-L-histidine (His-75) in 1 ml. of Media 199 at pH 6.0 for one hour at 37° C. Controls included the same amount of virus in Media 199 without poly-L-histidine under the same conditions and Media 199 with poly-L-histidine but no virus.

2. Four (4) female Balb/C mice approximately 10 weeks old were injected in the lower left jaw with 50 μl. of poly-L-histidine treated HSV1 (approximately $2.2 \times 10^5$ plaque forming units).

Four (4) mice (as above) were injected (as above) with 50 μl. of the virus control from Media 199 but lacking poly-L-histidine (approximately $2.2 \times 10^5$ plaque forming units).

Four (4) mice (as above) were injected (as above) with 50 μl. of the Media 199 containing poly-L-histidine but lacking virus (approximately 5 μg. poly-L-histidine per mouse).

3. All animals were observed daily for 14 days.

Results

The four (4) animals injected with poly-L-histidine treated HSV1 and the 4 animals injected only with poly-L-histidine remained healthy throughout the study.

The four (4) animals injected with the HSV1 control preparation were affected as follows:

Two (2) of the 4 mice died, one on day 7 and one on day 9 of the experiment. Of the two surviving mice, one showed severe symptoms of virus infection including swollen left eye, hair ruffling, crouching position, lack of mobility. However, this mouse survived and eventually recovered. The final mouse in this group showed minor symptoms including some swelling in the left eye and minor ruffling of the hair.

Conclusions

Poly-L-histidine inactivated HSV1 failed to cause disease in these animals. Thus, the inactivation is irreversible which is consistent with our in vitro studies and the peptide protected these animals from the disease. Also, the poly-L-histidine by itself caused no observable adverse effect when injected into the control animals.

---

TEST PROTOCOL

Methods: Stock solution — 10 mg. His-75/ml. 0.04M acetic acid
Medium 199 — Flow Laboratories
To 9.8 ml. of Media 199 add 0.1 ml. stock His-75 (final concentration 100 μg/ml.) (Tissue culture medium from Flow Laboratories, MD.)

↓ pH to 5, 6, 7, or 8 using 0.1N NaOH

↓

To 0.9 ml. of Media 199 containing 100 μg. His-75 at a pH of 5, 6, 7, or 8 is added 0.1 ml. of HSV1 or HSV2 containing approximately $10^5$ plaque forming units per milliliter (pfu/ml.).

TEST PROTOCOL

↓ incubate at the appropriate temperature for a defined period of time (e.g. 37° C./1 hr.).

↓ dilute the sample 100-fold.

↓ place 0.1 ml. of diluted sample on monolayer cultures of VERO cells

↓ adsorb virus 1 hour at room temperature with intermittent rotation

↓ overlay cultures with Media 199 containing 5% calf serum, 50 µg/ml. gentamycin, 0.23% $NaHCO_3$ and 0.5% methyl-cellulose

↓ place cultures in the incubator for 3 days (37° C., 5% $CO_2$, humid)

↓ stain the monolayers with 0.5% crystal violet in 70% EtOH

↓ count the plaques and compare poly-L-histidine treated samples with controls

↓ calculate % survivors as follows: $\frac{\text{(pfu treated virus)}}{\text{(pfu control virus)}} \times 100$

TABLE 1

Effect of various concentrations of His-75 on the inactivation of HSV-1 and HSV-2. HSV-1 or HSV-2 ($\sim 10^5$ pfu/ml) were incubated with various concentrations of His-75 at pH 6.0 for 1 hr at 37° C. Control preparations were treated in an identical manner but not exposed to His-75. The samples were diluted 100-fold and tested for surviving virus by the plaque assay.

| His-75 Concentraton (µg/ml) | Percent Survivors | |
|---|---|---|
| | HSV-1 | HSV-2 |
| 100 | 0 | 0 |
| 10 | 64 | 84 |
| 1 | 83 | 62 |
| 0.1 | 100 | 100 |

TABLE 2

The effect of pH shift on the inactivation of HSV-1. HSV-1 ($\sim 10^5$ pfu/ml) was exposed to His-75 at pH 6.0 at 37° C. for 30 minutes at which time the pH was rapidly adjusted to pH 7.2 and held an additional 30 minutes at 37° C. Other virus preparations were exposed to His-75 as above for 30 or 60 minutes while controls were treated identically but not exposed to His-75. The preparations were diluted 100-fold and tested for surviving virus by the plaque assay.

| His-75 | Percent Survivors |
|---|---|
| pH 6.0, 30 minutes → pH 7.2, 30 minutes | 0 |
| pH 6.0, 60 minutes | 0 |
| pH 6.0, 30 minutes | 0 |

We claim:

1. A method for reducing the transmissability of Herpes viral infection from a subject infected therewith which comprises topically adminstering a viricidally effective amount of poly-L-Histidine of between 24 and 500 amino acid residues, at a pH of less than 7 to a subject in need of same.

2. A method for reducing the transmissability of a Herpes viral infection from a first subject infected therewith to a second subject in contact with said first subject which comprises topically applying viricidally an effective amount of poly-L-Histidine of between 24 and 500 amino acid residues, at a pH of less than 7 to tissues of said first subject, at or proximate to the location of tissue lesions caused by said infection.

3. A method for reducing the transmissability of a Herpes viral infection from a subject infected therewith to a second subject in contact with said first subject which comprises topically applying a poly-L-Histidine of between 24 and 500 amino acid residues, at a pH of less than 7 to tissues of said second subject, at or proximate to a location likely to come into contact with the location of tissues of said first subject likely to have lesions caused by said infection.

4. A method for reducing the transmissability of a Herpes viral infection in a subject infected therewith to a different tissue location on said subject which comprises topically applying viricidally an effective amount of a poly-L-Histidine of between 24 and 500 amino acid residues comprising at least 24 residues of L-Histidine, at a pH of less than 7 to tissues of said subject, at or proximate to a location on said subject likely to have lesions caused by said infection.

5. A method of claim 1 wherein said peptide contains from 24 to about 75 L-Histidine residues.

6. A method of claim 1 wherein said administration is at a pH of between about 3 and about 6.8.

7. A method of claim 1 wherein said administration is at a pH of between about 5.0 and about 6.1.

8. A method of claim 1 wherein the administration is to the eye.

9. A method of claim 1 wherein the administration is to the oral cavity.

10. A method of claim 1 wherein the administration is by vaginal insertion.

11. A method of claim 1 wherein the administration is by anal insertion.

12. A method of claim 1 wherein the administration is by topical administration to the skin.

13. A method of claim 1 wherein the infection is caused by HSV1 or HSV2 virus.

* * * * *